US008685945B2

(12) United States Patent
Ketelson et al.

(10) Patent No.: US 8,685,945 B2
(45) Date of Patent: Apr. 1, 2014

(54) POLYMERIC ARTIFICIAL TEAR SYSTEM

(75) Inventors: Howard Allen Ketelson, Dallas, TX (US); James W. Davis, Argyle, TX (US); David L. Meadows, Collyville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 13/302,439

(22) Filed: Nov. 22, 2011

(65) Prior Publication Data

US 2012/0070402 A1 Mar. 22, 2012

Related U.S. Application Data

(63) Continuation of application No. 12/429,942, filed on Apr. 24, 2009, now abandoned.

(60) Provisional application No. 61/048,175, filed on Apr. 26, 2008.

(51) Int. Cl.
*A61K 31/70* (2006.01)
(52) U.S. Cl.
USPC .......................................................... 514/54
(58) Field of Classification Search
USPC .......................................................... 514/54
See application file for complete search history.

(56) References Cited

U.S. PATENT DOCUMENTS

| | | | |
|---|---|---|---|
| 4,136,173 | A | 1/1979 | Pramoda et al. |
| 6,403,609 | B1 | 6/2002 | Asgharian |
| 6,486,139 | B1 | 11/2002 | Cavallo et al. |
| 6,583,124 | B2 * | 6/2003 | Asgharian ........................ 514/54 |
| 2004/0253202 | A1 | 12/2004 | Chowhan et al. |
| 2009/0196845 | A1 * | 8/2009 | Xia et al. .................... 424/78.04 |

FOREIGN PATENT DOCUMENTS

| | | |
|---|---|---|
| GB | 1593954 | 7/1981 |
| WO | 99 06023 | 2/1999 |
| WO | 99 06070 | 2/1999 |
| WO | 2008 036855 | 3/2008 |

OTHER PUBLICATIONS

Aragona, et al., "Long Term Treatment With Sodium Hyaluronate-Containing Artificial Tears Reduces Ocular Surface Damage in Patients With Dry Eye," British J Ophthalmology, 2002, pp. 181-184, vol. 86.
Cheng, et al., "Characterization and Intermolecular Interactions of Hydroxypropyl Guar Solutions," Biomacromolecules, 2002, pp. 456-461, vol. 3.
Christensen, et al., "Evaluation of the Effect on Tear Film Break-Up Time Extension by Artificial Tears in Dry Eye Patients," Presented at: 23rd Biennial Cornea Research Conference; Oct. 3-4, 2003, Boston, MA.
D'Arienzo, et al., "A Comparison of Two Marketed Artificial Tears in Improvement of Tear Film Stability as Measured by Tear Film Break-Up Time (TFBUT) and Ocular Protection Index (OPI)," Poster Presentation, Tear Film and Ocular Surface Society Meeting, Taormina, Sicily, 2007.
Gifford, et al., "A Clinical Evaluation of Systane," Contact Lens Anterior Eye, 2006, pp. 31-40, vol. 29.
Kesavan, et al., "Rheology of Guar and HPG Crosslinked by Borate," Macromolecules, 1992, pp. 2026-2032, vol. 25.
Lane, et al., "An Evaluation of the In Vivo Retention Time of a Novel Artificial Tear as Compared to a Placebo Control," Poster Presentation, Association for Research in Vision and Ophthalmology Annual Meeting (ARVO) 2009.
Lemp, et al., "The Effect of Tear Substitutes on Tear Film Break-Up Time," IOVS, 1975, pp. 255-258, vol. 14.
Li, et al., "Viscoelasticity of Phospholipid Layers at Different Fluid Interfaces," Colloids and Surfaces A, 1999, p. 491, vol. 149.
Meyer, et al., "Tissue-on-Tissue Testing of Dry Eye Formulations for Reduction of Bioadhesion," Journal of Adhesion, 2006, pp. 607-627, vol. 82.
Miano, et al., "Insertion of Tear Proteins into a Meibomian Lipids Film," Colloids and Surfaces B: Biointerfaces, 2005, pp. 49-55, vol. 44.
Miano, et al., "Viscoelastic Properties of Insoluble Amphiphiles at the Air/Water Interface," J. Colloid Interface Science, 2006, pp. 269-275, vol. 296.
Nally, et al., "Ocular Discomfort and Tear Film Break-Up Time in Dry Eye Patients: A Correlation," IOVS, ARVO Abstract 2000, p. 1436, vol. 41(4).
Ousler, et al., "An Evaluation of Tear Film Break-Up Time Extension and Ocular Protection Index Scores Between Three Marketed Lubricant Eye Drops," Cornea, 2007, pp. 949-952, vol. 26(8).
Padday, et al., (Ed.), "Surface Tension. Part II. The Measurement of Surface Tension," Surface and Colloid Science, 1969, p. 101, vol. 1, Wiley-Interscience, New York.
Paugh, et al., "The Pre-Corneal Residence Time of Artificial Tears Measured in Dry Eye Subjects," Optometry of Visual Science, 2008, pp. 725-731, vol. 85(8).
Pezron, et al., "Reversible Gel Formation Induced by Ion Complexation. 1. Borax-Galactomannan Interaction," Macromolecules, 1988, pp. 1121-1125, vol. 21.
Pezron, et al., "Rheology of Galactomannan-Borax Gels," Journal of Poly. Science: Part B: Poly. Phys., 1990, pp. 2445-2461, vol. 28.
Pollard, et al., "Extension in Tear Film Break-Up Time After Instillation of HP-Guar Artificial Tear Substitute," IVOS, 2003, vol. 44 [E-Abstract 2489].
Torkildsen, et al., "Evaluation of Functional Visual Performance Using the IVAD Method with Currently Marketed Artificial Tear Products," Poster Presentation, Association for Research in Vision and Ophthalmology Annual Meeting (ARVO) 2009.

* cited by examiner

Primary Examiner — Elli Peselev

(57) ABSTRACT

The present invention relates to artificial tear formulations and ophthalmic formulations suitable for drug delivery. The formulations comprise galactomannans such as guar or hydroxypropyl guar and a borate source such as boric acid. The formulations further comprise a cis-diol such as sorbitol that interferes with the cross-linking of galactomannan and borate. Optionally, the formulations are substantially free of divalent cations.

13 Claims, 10 Drawing Sheets

POLYMERIC ARTIFICIAL TEAR SYSTEM

CROSS-REFERENCE TO RELATED APPLICATION

This application is a Continuation (CON) of U.S. Application Ser. No. 12/429,942, filed Apr. 24, 2009, now abandoned, priority of which is claimed under 35 U.S.C §120, the contents of which are incorporated herein by reference. This application also claims priority under 35 U.S.C. §119 to U.S. Provisional Patent Application No. 61/048,175, filed Apr. 26, 2008 the contents of which are incorporated herein by reference.

TECHNICAL FIELD OF THE INVENTION

The present invention relates to artificial tear formulations and formulations for ophthalmic drug delivery, and more specifically to galactomannan-borate polymer systems comprising a cis-diol.

BACKGROUND OF THE INVENTION

Many ophthalmic formulations comprise compounds that provide lubricity and other desirable properties. When these formulations are instilled in the eye, the properties of such compounds can prevent undesirable problems such as bioadhesion and the formation of friction-induced tissue damage, as well as encourage the natural healing and restoration of previously damaged tissues.

Many marketed artificial tear solution products contain polymers that display thixotropic and viscoelastic properties. Some of these polymers include hydroxypropylmethylcellulose, galactomannans such as guar and hydroxypropyl guar, carboxymethylcellulose, hyaluronic acid, and sodium alginate. The shear thinning and viscoelastic profiles of polymers play important roles when mixed with the tear film.

The retention profile, lubrication and mucomimetic properties of polymers in artificial tear solution products may play an important role by to helping stabilize the tear film and providing improved comfort to patients with dry eye disease. For example, the product Systane® (Alcon, Inc.) containing hydroxypropyl guar and the active ingredients polyethylene glycol 400 and propylene glycol has been reported by Paugh, et al. (2008) to be more effective at eliminating eye discomfort than similar viscosity enhancing polymers such as carboxymethyl cellulose.

The bulk rheology of polymers used in artificial tear solutions is often characterized by steady state shear (shear thinning) and dynamic oscillation tests (viscoelasticity). Although these tests are valuable, these bulk rheology experiments may not fully characterize the interfacial properties of such polymers. An understanding of the polymers' interfacial properties is critical, as these properties may play important roles in the interactions with tear film components at both the cornea/tear film interface and tear film/air interface. Another rheology test that can aid in understanding the dynamic and interfacial properties of polymers used in artificial tears is the oscillation drop experiment, described herein.

Ophthalmic formulations have been previously described that utilize galactomannan-borate gelling systems. U.S. Pat. No. 6,403,609 to Asgharian, entitled "Ophthalmic compositions containing galactomannan polymers and borate," describes such systems and is herein incorporated by reference in its entirety. The cross-linking of galactomannan and borate is responsible for the gel-forming behavior of the described formulations.

BRIEF SUMMARY OF THE INVENTION

The present invention generally relates to ophthalmic formulations comprising galactomannan, including galactomannans such as guar or hydroxypropyl guar. The formulations of the present invention also comprise a borate source such as boric acid. A cis-diol, such as sorbitol or propylene glycol, is present in the formulations and interferes with the cross-linking of the galactomannan and borate. The cis-diol is selected based on its diffusion characteristics relative to the galactomannan. Typically, the ophthalmic formulations of the present invention comprise a cis-diol that is a relatively small molecule such as sorbitol that diffuses more rapidly than the galactomannan in the ocular tear film. Upon instillation in the eye, the concentration of the cis-diol decreases at a different rate than the galactomannan, allowing the galactomannan and borate to cross-link a form a structured polymer network in situ. Thus, the gelling behavior and rheological characteristics of the formulations after instillation into the eye are controlled via selection of the cis-diol.

The formulations of the present invention are substantially free of divalent cations such as magnesium, zinc and calcium that can strengthen cross-linking of the galactomannan and borate. Once a formulation is instilled in the eye, divalent cations present in the tear film enhance formation of a structured galactomannan-borate polymer network.

The formulations of the present invention are also useful as drug delivery vehicles for ophthalmic therapeutics. Upon instillation of a formulation in the eye, a galactomannan-borate polymer network is formed; this network is able to hold various therapeutic agents on the eye, including demulcents.

The foregoing brief summary broadly describes the features and technical advantages of certain embodiments of the present invention. Additional features and technical advantages will be described in the detailed description of the invention that follows.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

Figure 8:
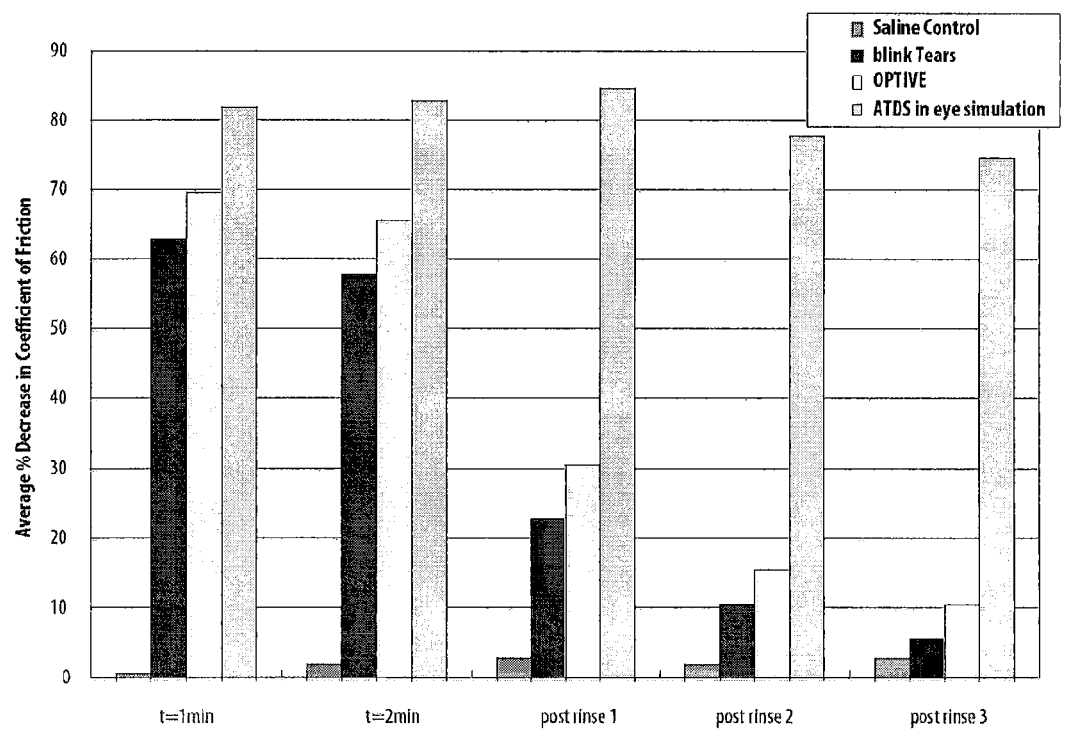
Figure 9:
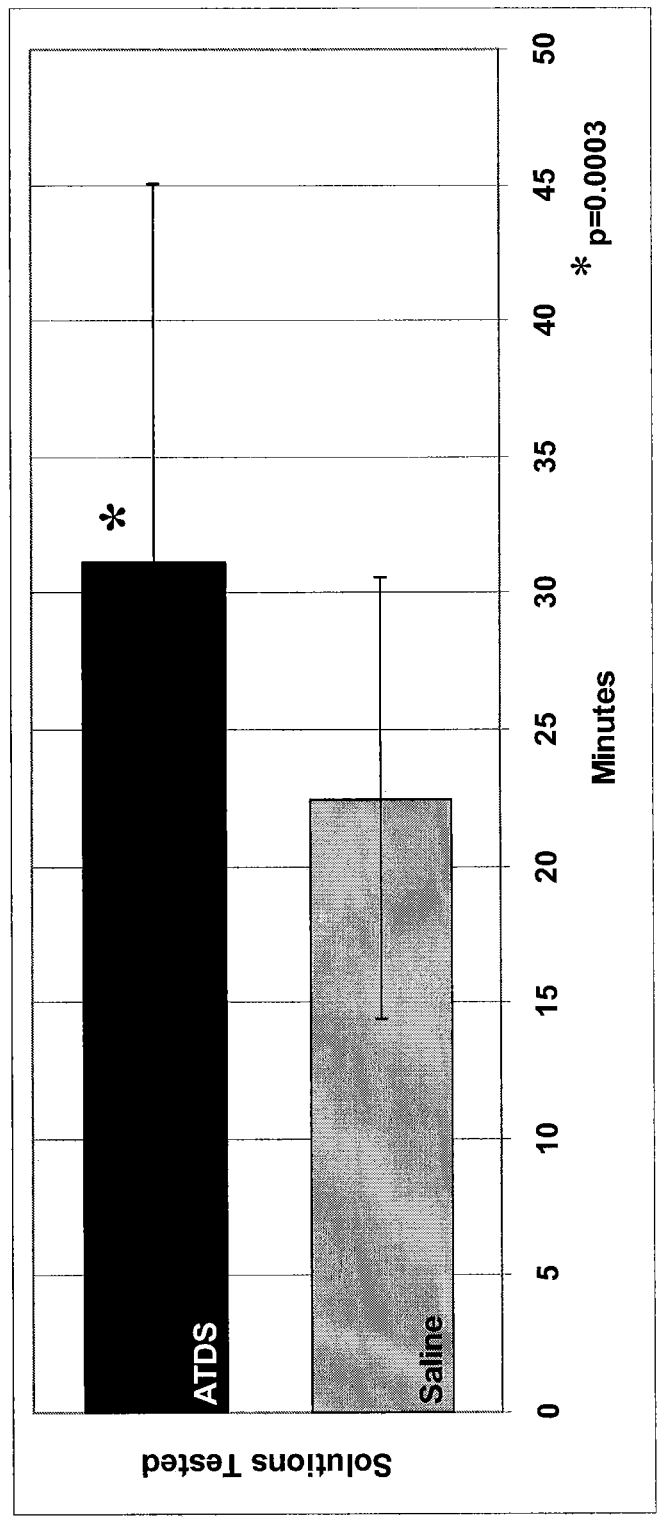
Figure 10:
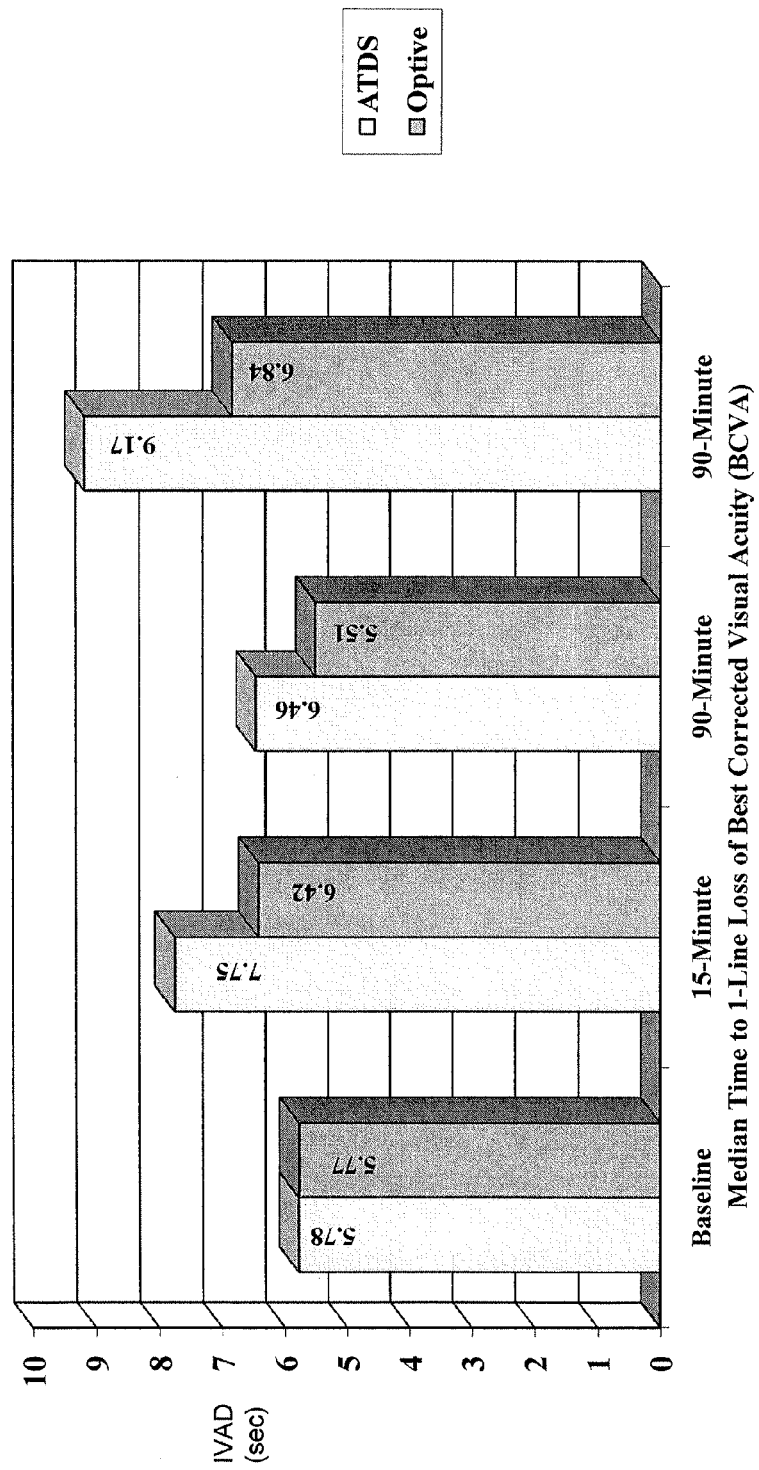

FIG. 8 is a graph of the average % decrease in coefficient of friction for test formulations, compared to baseline (Unisol®, saline control) at 1 & 2 minutes after application of formulation; and after each of 3 blot/Unisol® applications (post-rinses 1, 2 and 3) for saline control, OPTIVE®, blink Tears® and a galactomannan-borate formulation at pH 7.6 and without sorbitol;

FIG. 9 is a bar graph comparing the mean retention time of Unisol® saline control to a galactomannan-borate artificial tear formulation of the present invention; and FIG. 10 is a bar graph summarizing the result of a study comparing Optive® (a carboxymethylcellullose (CMC) and glycerin based artificial tear) and a galactomannan-borate artificial tear formulation of the present invention.

DETAILED DESCRIPTION OF THE INVENTION

Figure 1:
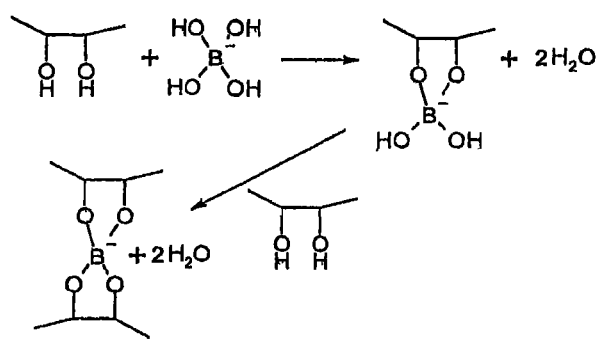
FIG. 1 is a diagram of the cross-linking behavior of borate and galactomannan.

The formulations of the present invention utilize a galactomannan-borate system in aqueous solution. A borate anion will condense onto the cis-diol groups of a galactomannan molecule, and may cross-link with a second galactomannan molecule as shown in FIG. 1. Cross-linking of borate and galactomannan is influenced by factors such as pH, among others, and such cross-linking in turn influences the viscosity of the solution. The present invention is directed to the use of cis-diols such as sorbitol and propylene glycol to interfere with the cross-linking of borate and galactomannan in ophthalmic formulations, thereby affecting the gelling and other rheological characteristics of the formulations. In the presence of cis-diols, borate and galactomannan exhibit reduced cross-linking behavior in aqueous solution, resulting in a lower solution viscosity. When used in a droppable ophthalmic formulation, the low viscosity solution has a reduced likelihood of causing unwanted effects on vision, such as blurring.

In a preferred embodiment of the present invention, the cis-diol sorbitol is used in galactomannan- and borate-containing formulations. Sorbitol is present at a first concentration that inhibits cross-linking of the galactomannan and borate. Once instilled in the eye, the sorbitol is diluted by the natural tear film allowing a gradual increase in the cross-linking of the galactomannan and borate and a corresponding gradual increase in viscosity and elasticity. This gradual increase in viscosity, cross-linking, and elasticity allows for effective spreading and less blurring upon contact, yet provides long lasting lubrication and corneal surface protection.

Divalent cations such as calcium generally interact with galactomannan and borate to strengthen cross-linking behavior. When present in galactomannan- and borate-containing formulations, divalent cations can increase the overall viscosity of such formulations. The formulations of the present invention are substantially free of divalent cations that would otherwise contribute to unwanted variations in galactomannan-borate cross-linking and, accordingly, formulation viscosity. Divalent cations include, but are not limited to, magnesium, calcium, and zinc cations. As used herein, the term "substantially free of divalent cations" means that the formulation contains divalent cation concentrations that do not interfere with the cross-linking of the galactomannan-borate polymer systems of the formulations. Generally, concentrations of divalent cations should be less than 5 parts per million to avoid interference with the galactomannan-borate polymer systems.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-β-D-mannopyranosyl units with α-D-galactopyranosyl units attached by (1-6) linkages. With the preferred galactomannans, the ratio of D-galactose to D-mannose varies, but generally will be from about 1:2 to 1:4. Galactomannans having a D-galactose:D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a formulation of the present invention at a concentration of about 0.01 to about 10 w/v %, preferably at about 0.1 w/v % to about 2.0 w/v %, and most preferably at about 0.16 to about 0.19 w/v %. Preferred galactomannans of the present invention are guar and hydroxypropyl guar.

The cis-diol compounds that may be used with embodiments of the present invention include, but are not limited to, hydrophilic carbohydrates such as sorbitol or mannitol that comprise cis-diol groups (hydroxyl groups attached to adjacent carbon atoms). Preferred cis-diol compounds of the present invention include polyethylene glycols, polypropylene glycols, and polyethyleneoxide-polybutyleneoxide block copolymers. Particularly preferred cis-diol compounds are sorbitol and mannitol. The cis-diol compounds are present at concentrations of about 0.5 to 5.0 w/v % in the formulations of the present invention, and are preferably present at a concentration of about 1.4%. The molecular weights of the cis-diol compounds are selected to ensure that the cis-diol diffuses and is eliminated from tear film at a faster rate than the galactomannan, allowing for increased galactomannan-borate cross-linking Generally, the molecular weight of such cis-diol compounds is between 400 g/mol to 5 million g/mol.

Borate is typically present at a concentration of about 0.2 to about 2.0 w/v %, and preferably at about 0.7 w/v %. As used herein, the term "borate" refers to all pharmaceutically suitable forms of borates, including but not limited to boric acid, and alkali metal borates such as sodium borate and potassium borate. Boric acid is the preferred borate used with embodiments of the present invention.

The borate compounds which may be used in the compositions of the present invention are boric acid and other pharmaceutically acceptable salts such as sodium borate (borax) and potassium borate. As used herein, the term "borate" refers to all pharmaceutically suitable forms of borates. Borates are common excipients in ophthalmic formulations due to good buffering capacity at physiological pH and well known safety and compatibility with a wide range of drugs and preservatives. Borates also have inherent bacteriostatic and fungistatic properties, and therefore aid in the preservation of the compositions.

The formulations of the present invention may optionally comprise one or more additional excipients and/or one or more additional active ingredients. Excipients commonly used in pharmaceutical formulations include, but are not limited to, demulcents, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants. Any of a variety of excipients may be used in formulations of the present invention including water, mixtures of water and water-miscible solvents, such as C1-C7-alkanols, vegetable oils or mineral oils comprising from 0.5 to 5% non-toxic water-soluble polymers, natural products, such as alginates, pectins, tragacanth, karaya gum, xanthan gum, carrageenin, agar and acacia, starch derivatives, such as starch acetate and hydroxypropyl starch, and also other synthetic products such as polyvinyl alcohol, polyvinylpyrrolidone, polyvinyl methyl ether, polyethylene oxide, preferably cross-linked polyacrylic acid and mixtures of those products.

Demulcents used with embodiments of the present invention include, but are not limited to, glycerin, polyvinyl pyrrolidone, polyethylene oxide, polyethylene glycol, propylene glycol and polyacrylic acid. Particularly preferred demulcents are propylene glycol and polyethylene glycol 400.

Suitable tonicity-adjusting agents include, but are not limited to, mannitol, sodium chloride, glycerin, and the like. Suitable buffering agents include, but are not limited to, phosphates, acetates and the like, and amino alcohols such as 2-amino-2-methyl-1-propanol (AMP). Suitable surfactants include, but are not limited to, ionic and nonionic surfactants, though nonionic surfactants are preferred, RLM 100, POE 20 cetylstearyl ethers such as Procol® CS20 and poloxamers such as Pluronic® F68.

The formulations set forth herein may comprise one or more preservatives. Examples of such preservatives include p-hydroxybenzoic acid ester, sodium perborate, sodium chlorite, alcohols such as chlorobutanol, benzyl alcohol or phenyl ethanol, guanidine derivatives such as polyhexamethylene biguanide, sodium perborate, polyquaternium-1, or sorbic acid. In certain embodiments, the formulation may be self-preserved so that no preservation agent is required.

Formulations of the present invention are ophthalmically suitable for application to a subject's eyes. The term "aqueous" typically denotes an aqueous formulation wherein the excipient is >50%, more preferably >75% and in particular >90% by weight water. These drops may be delivered from a single dose ampoule which may preferably be sterile and thus render bacteriostatic components of the formulation unnecessary. Alternatively, the drops may be delivered from a multi-dose bottle which may preferably comprise a device which extracts any preservative from the formulation as it is delivered, such devices being known in the art.

The formulations of the present invention are preferably isotonic, or slightly hypotonic in order to combat any hypertonicity of tears caused by evaporation and/or disease. This may require a tonicity agent to bring the osmolality of the formulation to a level at or near 210-320 milliosmoles per kilogram (mOsm/kg). The formulations of the present invention generally have an osmolality in the range of 220-320 mOsm/kg, and preferably have an osmolality in the range of 235-300 mOsm/kg. The ophthalmic formulations will generally be formulated as sterile aqueous solutions.

The compositions of the present invention can also be used to administer pharmaceutically active compounds. Such compounds include, but are not limited to, glaucoma therapeutics, pain relievers, anti-inflammatory and anti-allergy medications, and anti-microbials. More specific examples of pharmaceutically active compounds include betaxolol, timolol, pilocarpine, carbonic anhydrase inhibitors and prostglandins; dopaminergic antagonists; post-surgical antihypertensive agents, such as para-amino clonidine (apraclonidine); anti-infectives such as ciprofloxacin, moxifloxacin, and tobramycin; non-steroidal and steroidal anti-inflammatories, such as naproxen, diclofenac, nepafenac, suprofen, ketorolac, tetrahydrocortisol and dexamethasone; dry eye therapeutics such as PDE4 inhibitors; and anti-allergy medications such as H1/H4 inhibitors, H4 inhibitors, and olopatadine.

It is also contemplated that the concentrations of the ingredients comprising the formulations of the present invention can vary. A person of ordinary skill in the art would understand that the concentrations can vary depending on the addition, substitution, and/or subtraction of ingredients in a given formulation.

Preferred formulations are prepared using a buffering system that maintains the formulation at a pH of about 6.5 to a pH of about 8.0. Topical formulations (particularly topical ophthalmic formulations, as noted above) are preferred which have a physiological pH matching the tissue to which the formulation will be applied or dispensed.

In particular embodiments, a formulation of the present invention is administered once a day. However, the formulations may also be formulated for administration at any frequency of administration, including once a week, once every 5 days, once every 3 days, once every 2 days, twice a day, three times a day, four times a day, five times a day, six times a day, eight times a day, every hour, or greater frequency. Such dosing frequency is also maintained for a varying duration of time depending on the therapeutic regimen. The duration of a particular therapeutic regimen may vary from one-time dosing to a regimen that extends for months or years. One of ordinary skill in the art would be familiar with determining a therapeutic regimen for a specific indication.

The following examples are presented to further illustrate selected embodiments of the present invention.

EXAMPLES

Example 1 is a formulation according to an embodiment of the present invention. Examples 2 and 3 summarize studies performed on formulations according to embodiments of the present invention.

Example 1

| Ingredient | % w/v |
|---|---|
| Hydroxypropyl Guar | 0.16 to 0.19 |
| Boric Acid | 0.7 |
| Sorbitol | 1.4 |
| Polyethylene Glycol | 0.4 |
| Propylene Glycol | 0.3 |
| Potassium Chloride | 0.12 |
| Sodium Chloride | 0.1 |
| Polyquaternium-1 | 0.001 + 10% excess |
| 2-Amino-2-methylpropanol | 0.57 |
| Sodium Hydroxide/Hydrochloric Acid | q.s. pH 7.9 |
| Purified Water | q.s. 100% |

Example 2

Various solutions containing hydroxypropyl guar, borate and sorbitol were characterized in vitro to explore how the use of a cis-diol such as sorbitol can modify the bulk rheology, interfacial rheology and lubrication properties of hydroxypropyl guar-borate formulations. The experiments conducted show the effect of sorbitol in pH 7.9 formulations comprising a galactomannan-borate cross-linking system, and simulate the introduction of such formulations into the eye at a lower pH (7.6). Hydroxypropyl guar ($M_n=3\times10^6$ g/mol, polydispersity ratio (PD)=2-3) was used in the preparation of the artificial tear solution (ATDS) used in these experiments. The ATDS used for these experiments is the formulation of Example 1 above, pH adjusted to 7.9 or 7.6, and with varying concentrations of sorbitol.

Bulk rheology experiments were conducted using a controlled stress rheometer (AR 2000ex, TA Instruments, Inc.). The measurement system was a 40 mm acrylic 2° cone and plate with a sample volume of 0.58 mL. A temperature of 25° C.+/−0.1° C. was maintained and a cover was placed over the measurement system to prevent evaporation of the solutions. For Steady State Flow (SSF) experiments, the instrument applies a controlled stress which in turn gives the result as viscosity vs. shear rate. Two dynamic tests were conducted: oscillation stress sweep and oscillation frequency sweep. The oscillation stress sweep holds the frequency of the solution constant while measuring a range of stresses. The oscillation stress sweep measures G' (elastic/storage modulus) and G" (viscous, loss modulus). From this information the Linear Viscoelastic Region (LVR) can be determined. The LVR is a region in the stress sweep, obtained from G', where the solution holds its elasticity, G', over a range of stresses. A measure of relative elasticity, $\tan(\delta)=G"/G'$, is obtained from these experiments. The oscillation frequency sweep holds the stress constant within the LVR while measuring a range of frequencies. This measurement can determine G', G" and $\tan(\delta)$ as well. The oscillation frequency sweep shows how well a solution maintains its structure.

Interfacial rheology experiments were conducted using an optical oscillating drop generator device (OCA20, Dataphysics Instruments) equipped with a piezoelectric device and amplifier that controlled the oscillations of the drop. The drop, suspended in a temperature and humidity controlled cell at the tip of a stainless steel needle of 1.65 mm external diameter, was observed with a CCD camera (768×576 pixels) at 500 images per second. The oscillating drop generator (ODG) technique characterizes the mechanical strength of the films formed by analyzing the drop shape at a set frequency over a range of amplitudes. (See Li et al. (1999); Padday, et al. (1969); Miano et al. (2006); and Miano et al. (2005). The amplitude changes the volume and shape of the drop and therefore the surface area.

The dynamic interfacial tension was determined by analyzing the drop shape profile. The Young-Laplace model of a pendant drop of density ρ under gravity g, gives the surface tension γ by the following:

$$\lambda = \left(\frac{\rho g D_1^2}{H(s)}\right), s = \frac{D_1}{D_2}$$

Once the drop equilibrates, the drop volume is varied sinusoidally at a set frequency while the amplitude of the oscillation changes. This technique assumes that the surface tension of the drop remains uniform over the drop surface in the course of the dynamic variation of its surface. From this it is possible to determine the interfacial dilatational modulus E* according to the Gibbs equation:

$$E^* = -\frac{d\lambda}{d\ln(A)} = \mathrm{Re}|E1^*| + \mathrm{Im}|E1^*|$$

where Re|E1*| is the elastic modulus of the interface. The elastic modulus of the interface shows the significance of interface structure and is indicative of interfacial elastic properties. Im|E1*| is the loss modulus of the interface.

Friction screening experiments were conducted using a pin-on-disc tribometer with tissue-on-tissue (pericardium-on-pericardium) substrates using the method of Meyer et al. (2006). New tissue-tissue couples were used for all new solutions used in this study. The solutions used included Unisol® saline control (Alcon, Inc.), OPTIVE® (Allergan, Inc.), Blink® Tears (Abbott Medical Optics, Inc.) and the ATDS to simulate in-eye conditions (without sorbitol and at pH of 7.6). Of the four solutions tested, only the ATDS exhibits gelling behavior when applied to the eye. The apparatus conditions were set at 30 full cycles per minute for blink rate, 2.5 cm/seconds for blink velocity, and 8 kPa for blink pressure. The friction screening protocol comprised the following steps. First, a baseline measurement using 50 µl Unisol® saline control was made. Next, a simulation of solution spreading, wetting and initial retention to eye before rinsing and blinking was performed by applying 50 µl of the test formulation to the tissue. The tissue couple was then brought back into contact. Measurements were taken at 1 and 2 minutes post application, and following each of three tissue rinses with 50 µl Unisol®.

Results

Figure 2:
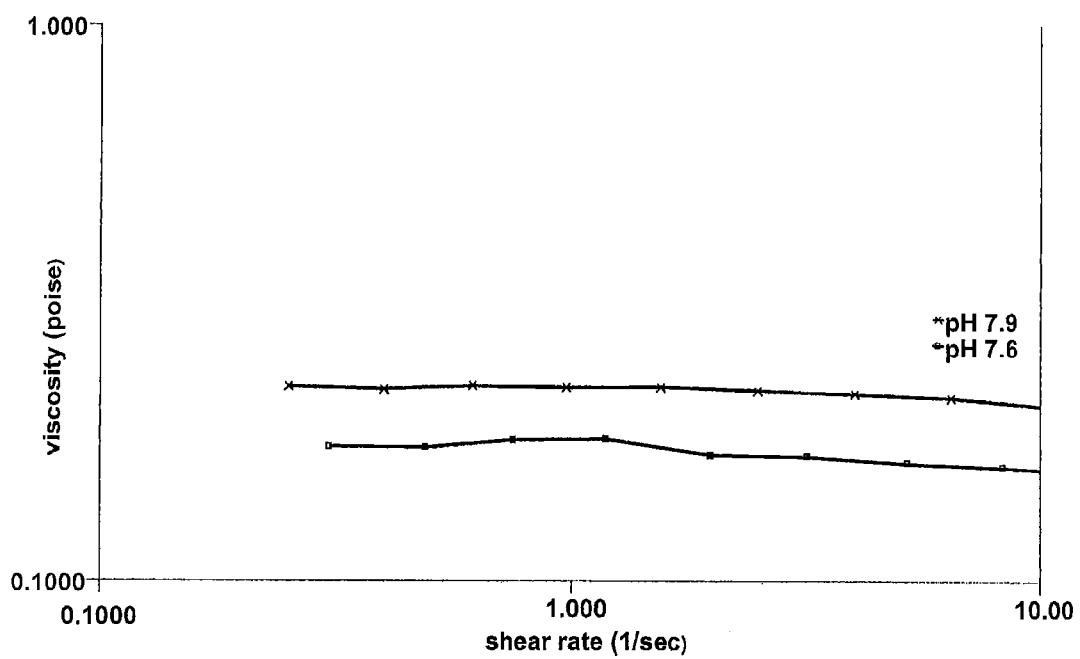
FIG. 2 is a graph showing steady state flow (SSF) viscosity as a function of shear rate for galactomannan-borate formulations at pH 7.9 and 7.6.

FIG. 2 is a graph showing steady state slow (SSF) viscosity as a function of shear rate for the ATDS at pH 7.9 and 7.6. The SSF data demonstrates that the viscosity decreased as the pH decreased from 7.9 to 7.6, and that the ATDS at pH 7.6 and 7.9 showed some shear thinning properties. Accordingly, the ATDS at pH 7.9 will shear thin when mixed with the tear film and through adjustment to a lower pH 7.6 there will be effective spreading and less blurring upon contact.

Figure 3:
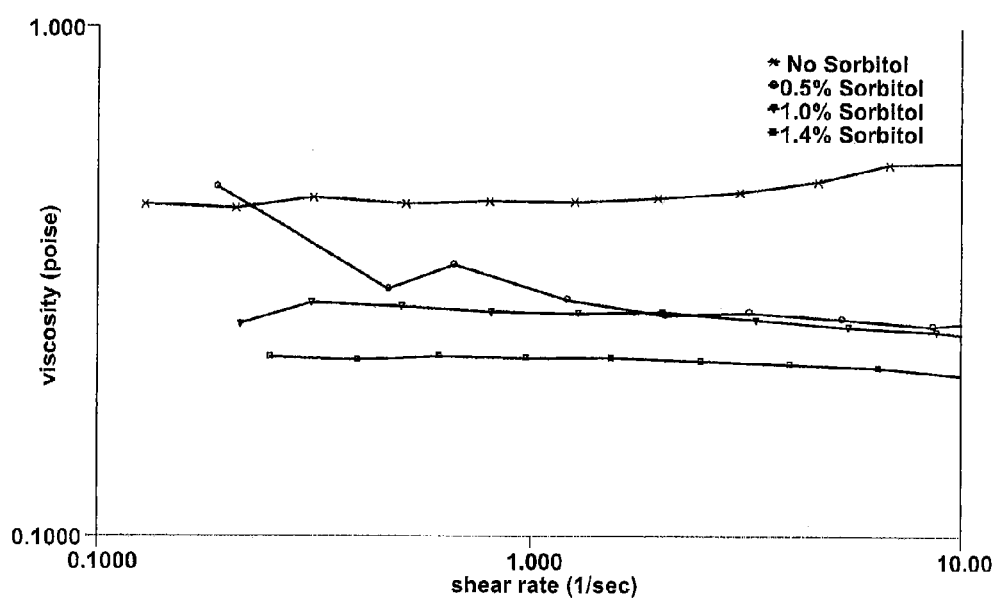
FIG. 3 is a graph showing steady state flow (SSF) vs. viscosity as a function of shear rate for formulations comprising 0.0 w/v %, 0.5 w/v %, 1.0 w/v % and 1.4 w/v % sorbitol.

FIG. 3 is a graph showing steady state flow (SSF) viscosity as a function of shear rate for the ATDS with 0.0 w/v %, 0.5 w/v %, 1.0 w/v %, and 1.4 w/v % sorbitol. The SSF data shows the modulation effect of sorbitol on the SSF flow properties of the ATDS, and that a reduction in sorbitol concentration leads to an increase in viscosity. FIG. 3 shows that as the sorbitol concentration of a galactomannan and borate solution increases, the measured viscosity of that solution decreases.

Figure 4:
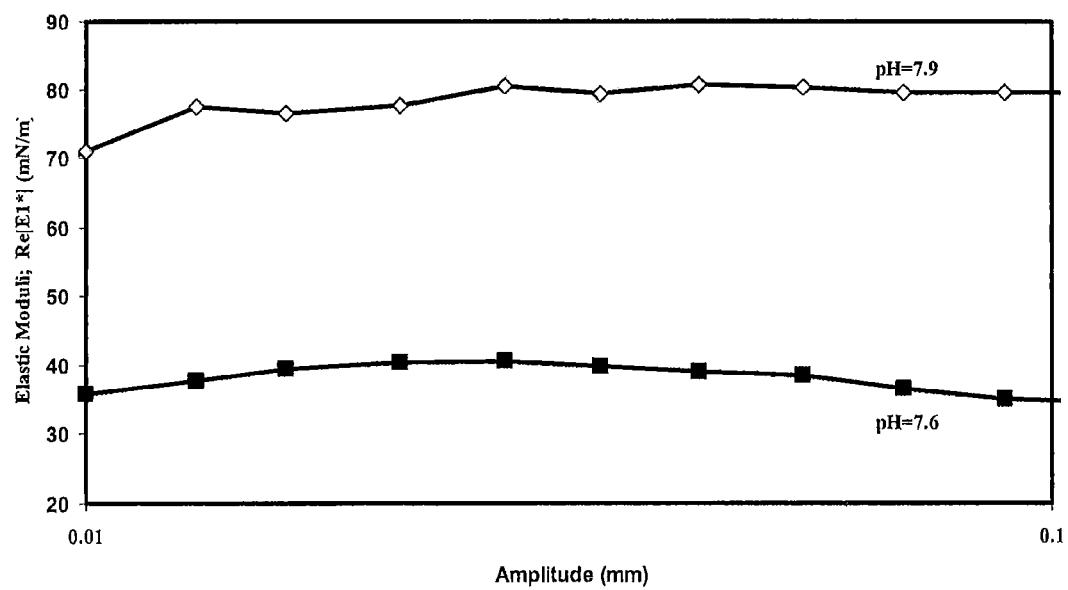
FIG. 4 is a graph showing oscillating drop amplitude sweep elastic moduli (Re|E1*|) as a function of amplitude of drop for a formulations at pH 7.9 and 7.6.

FIG. 4 is a graph showing oscillating drop amplitude stress sweep elastic moduli (Re|E1*|) as a function of amplitude of drop for the ATDS at pH 7.9 and 7.6. In these experiments, a high elastic moduli correlates to more structure at the water/air interface. The Stress Sweep data show the significance of the elastic contribution of the ATDS at the water/air interface. At both pH 7.9 and at pH 7.6, the ATDS was elastic dominant at the interface. This data indicates that the ATDS retained elastic structure despite its thinning and spreading characteristics demonstrated by the data presented in FIG. 2.

Figure 5:
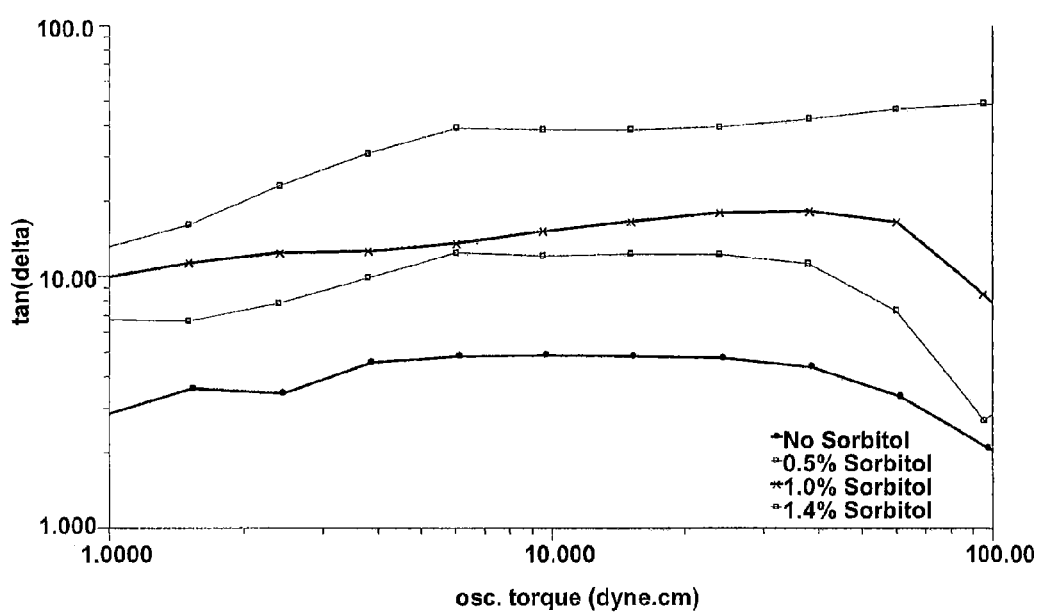
FIG. 5 is a graph showing stress sweep tan(δ) as a function of torque for formulations having 0.0 w/v %, 0.5 w/v %, 1.0 w/v % and 1.4 w/v % sorbitol.

FIG. 5 is a graph showing stress sweep $\tan(\delta)$ as a function of torque for the ATDS with 0.0 w/v %, 0.5 w/v %, 1.0 w/v % and 1.4 w/v % sorbitol. A low $\tan(\delta)$ correlates to more elasticity. A decrease in Sorbitol increases the elasticity of the ATDS. The formulation with no sorbitol has the most elasticity and the lowest $\tan(\delta)$. This experiment shows that polymer structure of a galactomannan borate solution increases through the dilution of sorbitol, which reflects the availability of more borate for galactomannan-borate cross linking.

Figure 6:
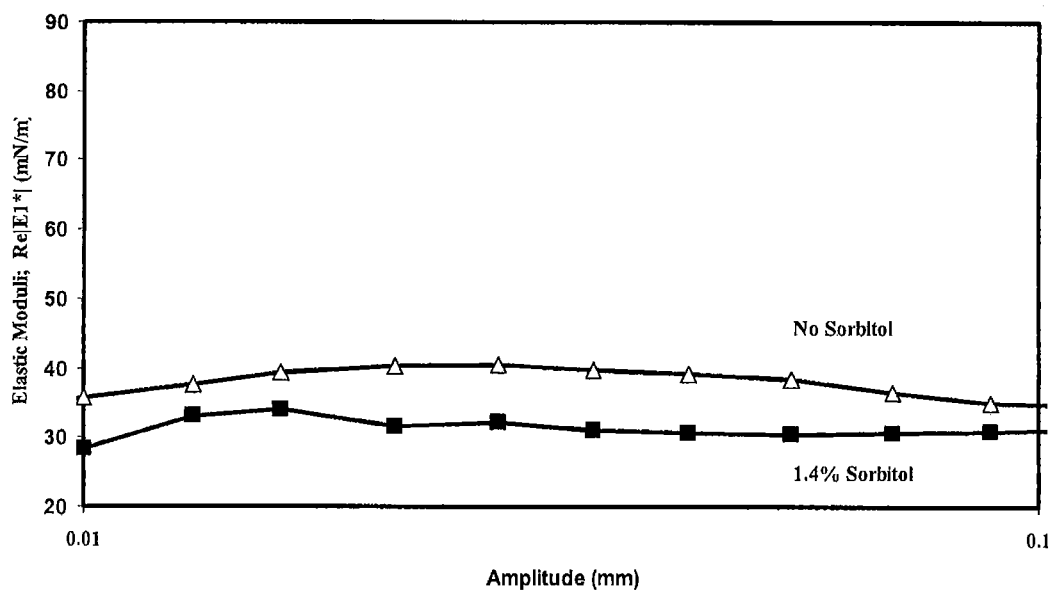
FIG. 6 is a graph showing oscillating drop amplitude sweep elastic moduli (RE|E1*|) as a function of amplitude of drop for a formulation having 0.0 w/v % and 1.4 w/v % sorbitol.

FIG. 6 is a graph showing oscillating drop amplitude sweep elastic moduli (RE|E1*|) as a function of amplitude of drop for the ATDS with 0.0 w/v % and 1.4 w/v % sorbitol. As with the FIG. 3 data, a high elastic moduli correlates to more structure at the interface. The experiment shows that dilution of sorbitol increases the surface elasticity of the ATDS. Further, the ODG data show that both ATDS's are elastic dominant and have gel-like properties at the aqueous/air interface.

Figure 7:
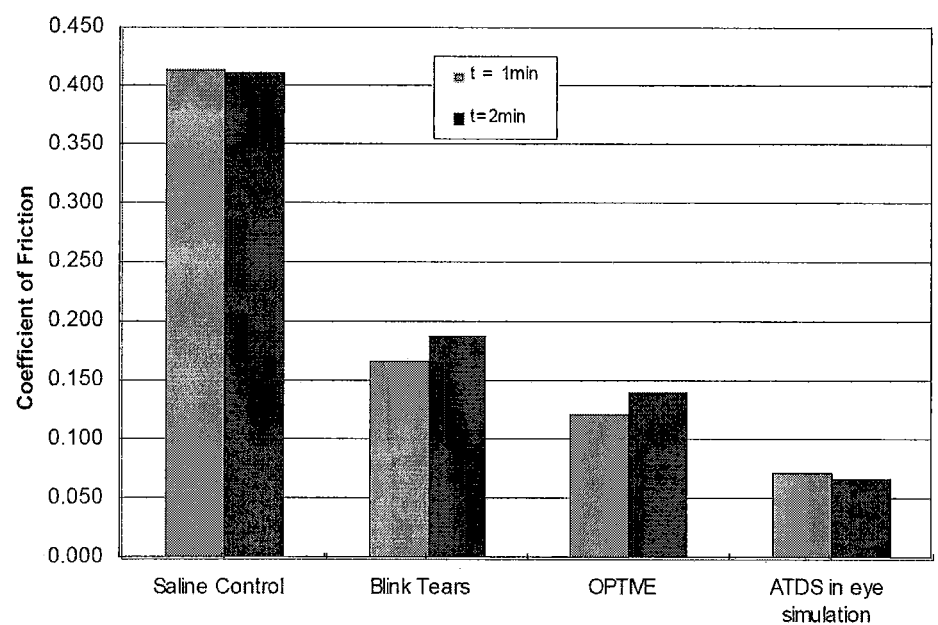
FIG. 7 is a graph showing the average coefficient of friction, 1 and 2 minutes after application to tissue in a friction screening model for saline control, OPTIVE®, blink Tears® and a galactomannan-borate formulation without sorbitol at pH 7.6 (to simulate conditions after application of the formulation to the eye)

FIG. 7 is a graph showing average coefficient of friction (Cof), 1 and 2 minutes after application of test solutions to the tissue in the friction screening model. The test solutions used were saline control, Optive®, blink Tears® and the ATDS in eye simulation solution (without Sorbitol, pH 7.6). The Cof data showed significant differences between the test solutions following measurement at times t=1 min and t=2 min. The saline control had the highest Cof for both t=1 min and t=2 min followed by blink Tears® and Optive®. The ATDS containing the active ingredients polyethylene glycol 400 and propylene glycol with hydroxypropyl guar showed the lowest Cof of the test solutions.

FIG. 8 is a graph showing average percent decrease in coefficient of friction, compared to baseline (Unisol®, saline control) at 1 & 2 minutes after application of formulation; and after each of 3 blot/Unisol® applications (post-rinses 1, 2 and 3) for saline control, Optive®, blink Tears® and the ATDS without sorbitol. The coefficient of friction (Cof) is a measurement of formulation lubricity on a surface. The Cof data show significant differences between the test solutions following the post-rinse cycles, and demonstrate the ability of the ATDS to maintain a low friction coefficient through the rinse cycles. For example, the % Cof data for the ATDS at t=1 min, t=2 min, post-rinse 1 and post-rinse 3 were 82%, 83%, 85% and 75%, respectively. The average % Cof at the post-rinse 3 timepoint for the saline control, blink Tears®, Optive® and the ATDS were 3%, 6%, 11% and 75%, respectively. The ATDS maintained the lowest Cof of the test solutions for the pericardium tissue substrates. The low Cof data upon application of the ATDS to the tissue substrates and persistence of the low Cof data following rinse cycles was believed to reflect the bulk and interfacial rheological properties of the ATDS, as shown in FIGS. 2-6.

Example 3

The ATDS formulation of Example 1 was compared in two in vivo studies against saline control solution (Unisol®) and the carboxymethylcellulose/glycerin formulation Optive®.

Retention Time Studies

An important measure of a lubricant eye drop is the assessment of ocular surface retention or swell time. The mean retention time of a galactomannan-borate solution of the present invention (the ATDS formulation of Example 1) was compared to a saline control solution (Unisol®) using a fluorophotometric technique. Briefly, a fluorescein labeled dextran tracer of approximately 70 kD (Molecular Probes, Eugene, Oreg.) was added to each test formulation at a concentration of 0.1 w/v %. A scanning fluorophotometer (Ocumetrics, Mountain View, Calif.) was used to monitor signal decay corresponding to elimination of the formulations. 25 dry eye patients were studied, and measurements were taken roughly every two minutes after application of the test formulation.

The results of the study, as reported by Lane et al. (2009), show that the ATDS formulation was retained significantly longer than the saline control solution (mean retention time of 31 minutes vs. 22 minutes for control). This statistically significant ($p=0.0003$) data is consistent with the in vitro studies above. For example, FIG. 8 shows that the ATDS maintains a low coefficient of friction (Cof) compared to other solutions (including Unisol® and Optive®) in vitro despite several washes simulating the effects of blinking. Thus, the rheological properties of the ATDS solution appear to result in superior retention time performance when applied to the eye.

Interblink Interval Visual Acuity Decay

The effects of dry eye on visual function can be assessed by testing interblink interval visual acuity decay (IVAD) using a real-time measurement of visual acuity degradation between blinks. FIG. 10 is a bar graph summarizing the result of a study comparing Optive® (a carboxymethylcellullose (CMC) and glycerin based artificial tear) and the ATDS formulation of Example 1.

In the study, 48 dry eye patients received both products in a randomized fashion with a 7-day washout between periods. Baseline measurements of IVAD, recorded as time (sec) that the patient could maintain best corrected visual acuity (BCA) within an interblink period were performed. Following a single drop of test solution, IVAD measurements were repeated at 15, 45, and 90 minutes.

As reported by Torkildsen et al. (2009), patients treated with the ATDS formulation had a significantly prolonged median time to a one-line loss of BCVA at 90 minutes post-instillation compared to the Optive® formulation. The ATDS formulation allowed a 58% increase in time at BCVA within the interblink period compared to baseline and was significantly longer (33%) than the CMC/glycerin Optive® formulation.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein may be utilized according to such related embodiments of the present invention. Thus, the following claims are intended to encompass within their scope modifications, substitutions, and variations to processes, manufactures, compositions of matter, compounds, means, methods, and/or steps disclosed herein.

REFERENCES

The following publications are incorporated herein by reference in their entirety:

Aragona P, Papa V, Micali A, Santocono M, Milazzo G, "Long term treatment with sodium hyaluronate-containing artificial tears reduces ocular surface damage in patients with dry eye", Br J Ophthalmology, Vol. 86:181-184, 2002.

Cheng Y, Brown K, Prud'homme R, "Characterization and Intermolecular Interactions of Hydroxypropyl Guar Solutions", Biomacromolecules, Vol. 3:456-461, 2002.

Christensen M, Stein J, Stone R, Meadows D, "Evaluation of the effect on tear film break-up time extension by artificial tears in dry eye patients", Presented at: 23rd Biennial Cornea Research Conference; Oct. 3-4, 2003; Boston, Mass.

D'Arienzo P, Ousler G, Schindelar M, "A comparison of two marketed artificial tears in improvement of tear film stability as measured by tear film break-up time (TFBUT) and ocular protection index (OPI)", Poster presentation, Tear Film and Ocular Surface Society Meeting 2007, Taormina, Sicily.

Gifford P, Evans B, Morris J, "A clinical evaluation of Systane", Contact Lens and Anterior Eye, Vol. 29:31-40, 2006.

Kasvan S, Prud'homme R, "Rheology of guar and HP-guar crosslinked by borate", Macromolecules, Vol. 25:2026-2032, 1992.

Li J, Kretzschmar G, MillerR, Mohwald H, Colloids and Surfaces A, Vol. 149:491, 1999.

Lane S, Webb J, Paugh J, Christensen M, "An evaluation of the in vivo retention time of a novel artificial tear as compared to a placebo control", Poster Presentation, Association for Research in Vision and Ophthalmology Annual Meeting (ARVO) 2009.

Lemp M, Goldberg M, Roddy M, "The effect of tear substitutes on tear film break-up time", IOVS, Vol. 14: 255-258, 1975.

Meyer A, Baier R, Chen H, Chowhan M, "Tissue-on-Tissue Testing of Dry Eye Formulations for Reduction of Bioadhesion", J Adhesion, Vol. 82:607-627, 2006.

Miano F, Winlove C, Lambusta D, Marletta G, "Viscoelastic properties of insoluble amphiphiles at the air/water interface", J. Colloid Interface Sci., Vol. 296:269-275, 2006.

Miano F, Calcara M, Millar T, Enea V, "Insertion of tear proteins into a meibomian lipids film", Colloids and Surfaces B: Biointerfaces, Vol. 44:49-55, 2005.

Nally L, Ousler G, Abelson M, "Ocular discomfort and tear film break-up time in dry eye patients: a correlation", IOVS, Vol. 41(4):1436. 2000 ARVO Abstract Ousler G, Michaelson C, Christensen M, "An Evaluation of Tear Film Break-up Time Extension and Ocular Protection Index Scores between Three Marketed Lubricant Eye Drops", Cornea, Vol. 26(8):949-952, 2007.

Padday J, Matijevic E, (Ed.), Surface and Colloid Science, Vol. 1:101, Wiley-Interscience, New York, 1969.

Paugh J, Nguyen A, Ketelson H, Christensen M, Meadows D, "The pre-corneal residence time of artificial tears measured in dry eye subjects", Optometry of Vision Science, Vol. 85(8):725-731, 2008.

Pezron E, Ricard A, Lafuma F, Audebert R, "Reversible gel formation induced by ion complexation. 1. Borax-galactomannan interaction", Macromolecules, Vol. 21:1121-1125, 1988.

Pezron E, Ricard A, Leibler L, "Rheology of Galactomannan-Borax Gels", Journal of Poly. Science: Part B: Poly. Phys., Vol. 28:2445-2461, 1990.

Pollard S, Stone R, Christensen M, Ousler G, Abelson M, "Extension in tear film break-up time after instillation of HP-guar artificial tear substitute", IOVS, Vol. 44, 2003 [E-Abstract 2489].

Torkildsen G, Martin A, Tudor M, Griffin J, Ousler G, Welch D, Abelson M, "Evaluation of functional visual performance using the IVAD method with currently marketed artificial tear products", Poster Presentation, Association for Research in Vision and Ophthalmology Annual Meeting (ARVO) 2009.

What is claimed is:

1. An ophthalmic formulation comprising a galactomannan, borate, and a cis-diol, wherein said formulation is substantially free of divalent cations and wherein said galactomannan is present at a concentration of 0.16 w/v % to 0.19 w/v% and said borate is present at a concentration of 0.7 w/v %, and wherein said cis-diol is sorbitol at a concentration of 0.5 to 5.0 w/v %, and wherein said galactomannan is selected from the group consisting of guar, hydroxylpropyl guar, and combinations thereof.

2. A formulation according to claim 1 wherein said cis-diol is present at a concentration of 1.4 w/v %.

3. A formulation according to claim 1 wherein said borate is boric acid.

4. A formulation according to claim 1 further comprising a demulcent selected from the group consisting of:
   glycerin, polyvinyl pyrrolidone, polyethylene oxide, polyethylene glycol, propylene glycol, polyacrylic acid, and combinations thereof.

5. A formulation according to claim 4 wherein said demulcent is polypropylene glycol or polyethylene glycol.

6. In an ophthalmic formulation comprising a galactomann and borate, the improvement comprising adding a cis-diol to prevent galactomann and borate cross-linking, thereby reducing the viscosity of the formulation, and wherein said cis-diol is sorbitol at a concentration of 0.5 to 5.0 w/v %.

7. A formulation according to claim 6, said formulation further being substantially free of divalent cations, thereby reducing the viscosity of the formulation.

8. A method for lubricating the eye comprising administering to the eye a formulation of claim 1.

9. A method for delivering a pharmaceutically active agent to the eye comprising:
   administering to the eye a formulation of claim 1 further comprising a pharmaceutically active agent.

10. An improved ophthalmic formulation comprising galactomannan and borate, said formulation comprising a cis-diol that is eliminated from tear film more rapidly than said galactomannan when the formulation is instilled in an eye and wherein said galactomannan is present at a concentration of 0.16 w/v % to 0.19 w/v % and said borate is present at a concentration of 0.7 w/v %, and wherein said cis-diol is sorbitol at a concentration of 0.5 to 5.0 w/v %, and wherein said galactomannan is selected from the group consisting of guar, hydroxylpropyl guar, and combinations thereof.

11. An improved ophthalmic formulation according to claim 10, said formulation further being substantially free of divalent cations, thereby reducing the viscosity of the formulation.

12. An improved ophthalmic formulation according to claim 10, said formulation further comprising a demulcent selected from the group consisting of:
   glycerin, polyvinyl pyrrolidone, polyethylene oxide, polyethylene glycol, propylene glycol, polyacrylic acid, and combinations thereof.

13. An ophthalmic formulation according to claim 1, said formulation having an osmolality of 220-320 mOsm/kg.

* * * * *